United States Patent
Trainer

[19]

[11] Patent Number: 6,094,266
[45] Date of Patent: Jul. 25, 2000

[54] DETECTOR FOR DETERMINING PARTICLE SIZE DISTRIBUTION IN AN OSCILLATING FLOW FIELD

[75] Inventor: Michael N. Trainer, Telford, Pa.

[73] Assignee: Honeywell Inc., Morristown, N.J.

[21] Appl. No.: 09/236,146

[22] Filed: Jan. 22, 1999

[51] Int. Cl.[7] .................................................. G01N 15/02
[52] U.S. Cl. ........................ 356/336; 73/61.48; 356/342
[58] Field of Search .................................... 356/336, 342, 356/349, 345, 340; 73/61.48, 61.69, 629

[56] References Cited

U.S. PATENT DOCUMENTS

| | | | |
|---|---|---|---|
| 4,147,059 | 4/1979 | Fathauer | 73/861.25 |
| 4,909,081 | 3/1990 | Kulczyk et al. | 73/597 |
| 5,453,837 | 9/1995 | Naqwi et al. | 356/357 |
| 5,739,432 | 4/1998 | Sinhba | 73/579 |

*Primary Examiner*—Frank G. Font
*Assistant Examiner*—Layla Lauchman
*Attorney, Agent, or Firm*—Anthony Miologos

[57] ABSTRACT

A detector used in a measurement system that determines the size distribution of particles contained in a dispersant medium is disclosed that includes means for exciting the dispersant medium at an ultrasonic frequency to cause particles contained in the dispersant medium to oscillate at the applied ultrasonic frequency. The detector of the present invention further includes a light source for producing light energy in a specific frequency range, a first light guide for conveying the light energy from the light source to the dispersant medium, a second light guide for capturing and conveying the light energy scattered by the particles in oscillation and a third light guide for conveying light energy from said light source to the second light guide to produce heterodyned light energy. A light energy detection device optically connected to the second light guide receives the heterodyned light energy and produces signals representative of the heterodyned light energy detected.

25 Claims, 6 Drawing Sheets

DETECTOR FOR DETERMINING PARTICLE SIZE DISTRIBUTION IN AN OSCILLATING FLOW FIELD

BACKGROUND OF THE INVENTION

1. Field of the Invention

The present invention relates generally to the field of determining particle size distribution and more specifically to an optical detector used for the measurement of particle size distribution in an oscillating flow field.

2. Discussion of the Related Art

The measurement of particle size distribution finds use in the process industries in the manufacture of pharmaceuticals, chemicals, abrasives, ceramics, pigments and the like, where the particle size affects the quality of the manufactured product.

A number of methods presently exist for determining the size distribution of particulate material for particles in the approximate size range of 0.1 to 1000 microns in diameter. The conventional method of measurement at high concentration is dynamic light scattering, as taught by U.S. Pat. No. 5,094,532 to Trainer et al, patented Mar. 10, 1992. This patent discloses a fiber optic Doppler anemometer and method that directs a beam of light into a scattering medium that contains particles in Brownian motion. The frequency of the scattered light is compared to non-scattered light emitted from the scattering medium and results in the generation of a first signal having a magnitude that is indicative of the difference in frequency between the scattered light and the non-scattered light. A second signal is generated having a magnitude that varies with frequency on a linear scale. The frequency scale of the second signal is then translated into a logarithmic scale and deconvolved to determine the size and distribution of moving particles within the scattering medium. The translation and deconvolving requires translation of analog signals to digital signals and subsequent processing by a central processor and a vector signal processor using fast Fourier transfer techniques (FFT). In order to solve for a known particle size distribution of over 80 particle diameters the method just described must sample over 80 frequencies. Even though this method provides an accurate measurement of particle size distribution, it does require a long time period (usually greater than two minutes) to process all of the sample frequencies, due primarily to the stochastic nature of Brownian motion. This technique is best suited for use in a laboratory with samples that have been extracted from a process and properly prepared for measurement analysis. Additionally, this method is strongly dependent upon dispersant viscosity and temperature and the use of non-flowing sample delivery systems. Although this technique provides accurate results for particles having diameters less than 1 micron, it exhibits poor size and volume accuracy for particles greater than 1 micron.

Another recognized technique and method for measuring the size distribution of very small particles is static light scattering, or angular light scattering. In this method, a collimated monochromatic light beam irradiates an ensemble of particles that flow perpendicularly through the collimated light beam. Light scattered from the particles emerges from the interaction over a range of angles from the axis of the collimated beam. The scattered light is collected by a lens placed in the path of the scattered light. The scattered light patterns focused in the focal plane of the lens are typically measured by an array of photodetectors placed in the focal plane. The angular extent of the scatter pattern is determined by the size of the particles. The smaller the particle, the wider the angular extent of the scatter; the larger the particle, the narrower the angular extent of the scatter.

One such method is taught by U.S. Pat. No. 5,416,580 to Trainer, patented on May 16, 1998, which uses multiple light beams to irradiate the particles. This method has demonstrated excellent measurement results for particles in the 0.1 to 3000 micron range in flowing sample systems, without temperature or viscosity dependency. Unlike the dynamic scattering techniques, measurements can be made in less than five seconds with repeatability superior to that of the dynamic light scattering. However, in order to produce good measurement accuracy for a process sample at a high concentration, for example 10% by volume, the process sample must be properly diluted with a dispersant medium to minimize the particle concentration.

Each of the above described techniques is limited to a certain range of particle size, concentration and shape. Particles of many shapes are encountered in the aforementioned industrial processes. In certain applications hydrodynamic particle size measurement techniques present a better correlation to the product quality than the optical particle size measuring techniques for irregularly shaped particles. A particularly difficult region is between 0.5 and 1 microns, where both static and dynamic scattering can present somewhat of a less than accurate measurement of particle size distribution. Hydrodynamic particle size measurement techniques employ a basic concept of detecting a particle's motion, or oscillations, in a fluid dispersant caused by a vibrating surface or an ultrasonic wave. Depending on the oscillating frequency applied to the dispersant fluid, the particles will closely follow the oscillation of the dispersant fluid. The present invention contemplates the use of optical light scattering techniques for measuring the Doppler shifted light that is scattered by particles suspended in a dispersant medium and which are excited by an ultrasonic wave. The motion of the particles and dispersing fluid are compared as a function of excitation frequency to provide a determination of particle size distribution.

BRIEF SUMMARY OF THE INVENTION

It is, therefore, an object of the present invention to provide an optical detector arranged to be used in a measurement system for the accurate measurement of particle size distribution and which employs an oscillating flow field.

In accordance to the object of the present invention, a detector used in a measurement system that determines the size distribution of particles contained in a dispersant medium is disclosed, comprising a housing having a head end with the head end substantially immersed in the dispersant medium. Means for exciting the dispersant medium at an ultrasonic frequency are housed within the head end and are arranged to cause the particles contained in the dispersant medium to oscillate at the applied ultrasonic frequency.

The detector further includes an optical device housed within the housing. The optical device includes a light source that produces light energy in a specific optical frequency range. A first light guide is optically coupled to the light source and conveys the light energy from the light source to the head end and into the dispersant medium. A second light guide captures and conveys into the second light guide the light energy scattered by the particles in oscillation. A third light guide optically couples the first light guide to the second light guide and conveys the light energy from the light source to the second light guide, producing heterodyned light energy.

A light energy detection device optically connected to the second light guide receives the heterodyned light energy and, responsive to the received heterodyned light energy, produces signals representative of the received heterodyned light energy. The measurement system receives the detector's output signals, which are converted to digital signals by A/D conversion techniques. The digital signals are subsequently processed by a programmable computing device using well-known inversion techniques to obtain the desired particle size distribution.

A second embodiment of the detector just described is disclosed that includes a second light detection device optically connected to a fourth light guide. The fourth light guide couples the scattered light energy from the second light guide directly to the second light detection device. The second light detection device produces a second signal representative of the particle scattered light detected. The heterodyne output signal from the first light detection device and the output signals from the second light detection device are converted into digital signals by A/D conversion techniques and applied to a computer for processing. Since the demodulated signals are relatively linear, they are easily solved by an iterative constrained inversion algorithm by the measurement system computer, based on a theoretical model of particle motion in an oscillating dispersant.

BRIEF DESCRIPTION OF THE SEVERAL VIEWS OF THE DRAWINGS

Other objects, features, and advantages of the present invention will be apparent from the following description of a preferred embodiment thereof, taken in conjunction with the sheets of drawings, in which.

DETAILED DESCRIPTION OF THE INVENTION

The degree to which a particle will follow dispersant motion depends upon ultrasonic wave frequency, particle size, particle and dispersant density and viscosity. Particles will accurately follow the ultrasonic motion of the dispersant at low frequencies. However, at certain higher frequencies the relative amplitude and phase between particle and dispersant motion will change. The phenomena of particle motion relative to dispersant motion is graphically shown in FIG. 1, where the particle-to-dispersant density ratio is 1.2 and dispersant viscosity is 1 centipoise. The data represents particle diameters between 0.25 and 32 microns, over a liquid or dispersant frequency range from 10 Hz to 100 Mhz. Each particle size represented has a frequency range transition region where below this region the particle follows closely the oscillation of the dispersant and above this region the particle motion is attenuated, relative to the motion of the dispersant. This relationship between the motion of the particle and dispersant can be described as a linear system with a complex frequency response.

The present invention contemplates the use of a detection device that is used to sense the Doppler broadened spectrum of light scattered by the particles in oscillation.

Figure 2:
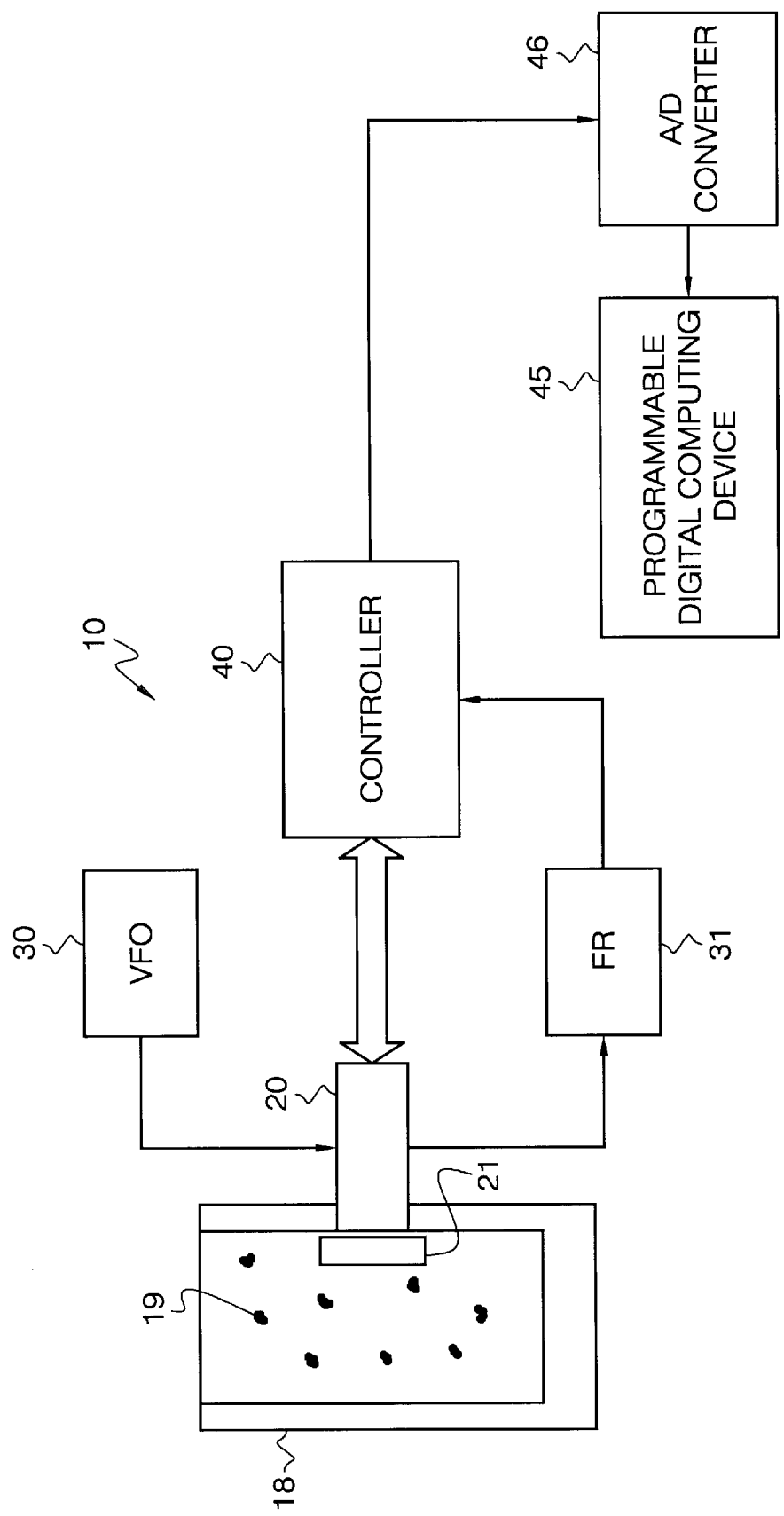
FIG. 2 depicts, in block diagram view, a measurement system used with the present invention.

Referring to FIG. 2, a measuring system 10 is shown that uses the detection device of the present invention. The system 10 is comprised of an optical detector 20 having a head end 21 submerged into a sample cell 18 that contains the particulate matter 19 suspended in a scattering medium, such as water. The particulate scattering medium may be selected from a wide range of media as long as it is inert with respect to the particulate matter suspended therein. Even though optical detector 20 is shown immersed into a sampling cell 18 that is isolated from a manufacturing process, it will be well understood by those skilled in the art that the cell 18 could be part of an apparatus which extracts representative samples of the manufactured product withdrawn from a conduit transporting the product from one stage of the manufacturing process to another. The prepared sample can be automatically delivered to the cell 18 or delivered on a demand basis. A Variable Frequency Oscillator (VFO) 30 and a Frequency Receiver (FR) 31 are connected to optical detector 20. The VFO 30 is used to drive an ultrasonic transducer transmitter located on the optical detector and the FR 31 receives signals representing the ultrasonic frequencies received by an ultrasonic transducer receiver also located on the detector. A controller 40 is connected to optical detector 20 and provides electrical signals to drive a laser diode and to receive signals from a light energy detection device, both located within the detector 20. The signals representing the detected particle size distribution are converted to digital signals by A/D conversion techniques by an A/D converter 46 and subsequently processed by a programmable computing device 45 by using well-known inversion techniques to obtain the desired particle size distribution.

Figure 3:
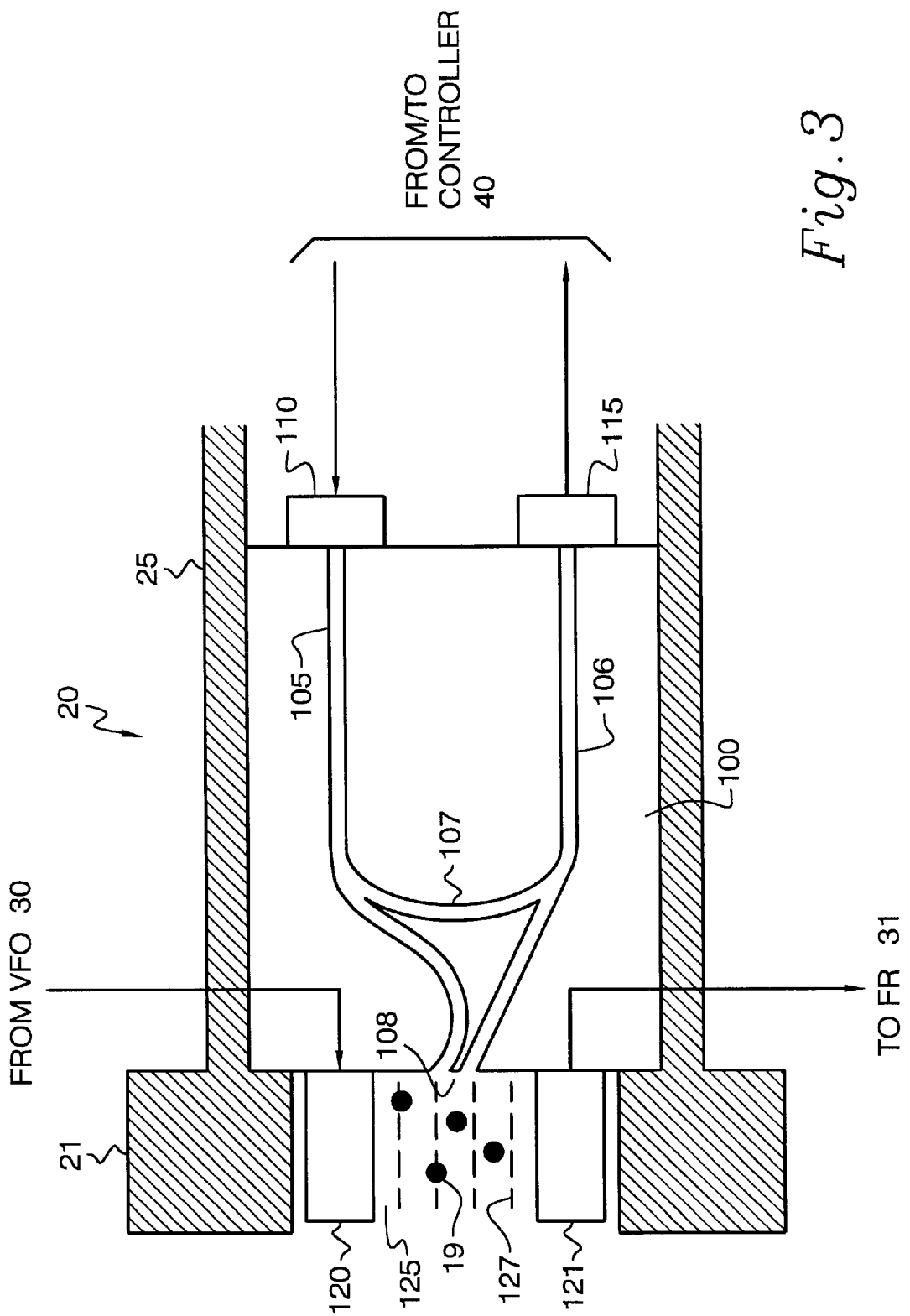
FIG. 3 depicts the first embodiment of the detector of the present invention.

Turning now to FIG. 3 of the included drawings, a first embodiment of the optical detector 20 of the present invention is illustrated. The optical detector 20 includes an integrated optic device 100 located internally within a housing 25 of the optical detector 20. The integrated optic device 100 further includes a laser diode 110 optically connected to a first optical waveguide 105. A second optical waveguide 106 is optically connected to a light energy detection device 115. Laser diode 110 and light energy detection device 115 are further electrically connected to controller 40. Optical waveguides 105 and 106 converge proximate to each other at point 108 located at an edge of the integrated optics device 100 and within head end 21.

An ultrasonic transducer transmitter 120, such as a piezoelectric transducer, extends from integrated optics device 100 within head end 21. An ultrasonic transducer receiver 121 also extends from the integrated optic chip 100 and is arranged in a spaced and facing relationship with the ultrasonic transducer transmitter 120, forming a detection area 125 therebetween. Transmitter 120 is electrically connected to VFO 30 which drives transmitter 120 at various frequencies from a few Hertz to the Megahertz range. The receiver 121 is electrically connected to the FR 31 and is disposed to detect and track the amplitude and phase of the ultrasonic waves 127 transmitted into detection area 125. Ultrasonic waves 127 transmitted from transducer 120 travel through detection area 125 and excite particles 19 contained therein into oscillation.

Figure 4:
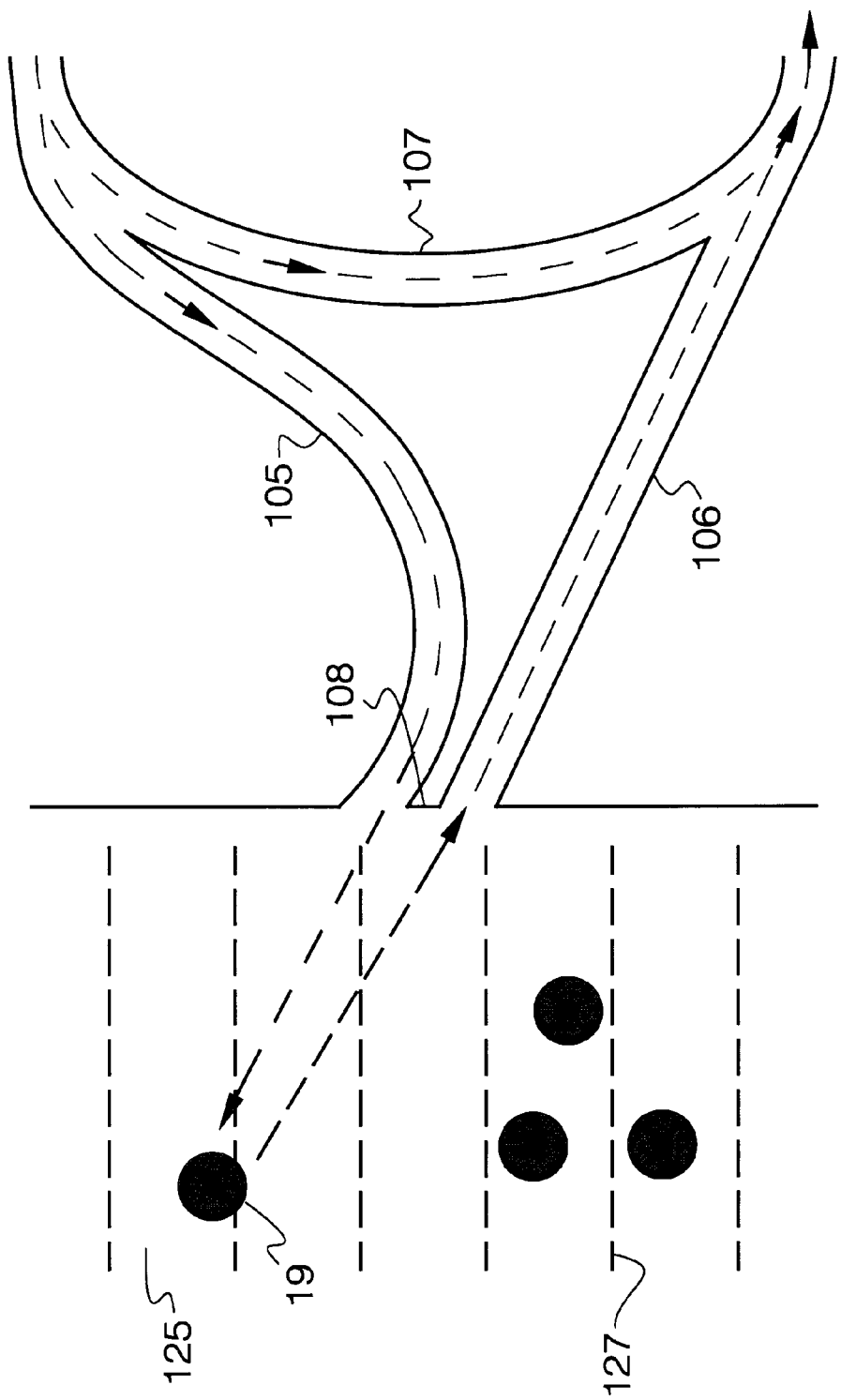
FIG. 4 depicts, in diagram view, the irradiation of the particles and collection of the scattered light energy from the particles in an oscillating flow field in accordance with the first embodiment of the present invention.

With reference to FIG. 3 and FIG. 4, upon the application of excitation voltage from controller 40, laser diode 110 produces light energy in a specific optical frequency range that is optically coupled into waveguide 105. The light coupled into waveguide 105 exits the waveguide from a first port at point 108 and is injected into the detection area 125 to irradiate particles 19 contained therein. The Doppler shifted light scattered by the oscillating particles 19 is collected by waveguide 106 from a second port at point 108 and conveyed to light energy detection device 115.

In order to measure the Doppler broadened spectrum light scattered by particles 19, it must be mixed with the source light produced by laser diode 110. This is accomplished by optical loop 107. Optical loop 107 acts as a local oscillator to heterodyne or mix the laser source light from waveguide 105 (no Doppler frequency shift) with the Doppler-shifted scattered light collected by waveguide 106. This produces a down-shifted difference light spectrum similar to that commonly used in dynamic light scattering techniques. However, unlike conventional dynamic light scattering, this down-shifted signal has a deterministic frequency modulated spectrum instead of a Brownian stochastic spectrum. This provides more reproducible size determinations in less time than when using the more common dynamic light scattering techniques.

The velocity and particle size information retrieved by the light detection device 115 is passed as detector current to the controller where it is demodulated at various ultrasonic excitation frequencies. The total demodulated particle velocity amplitude spectrum is the sum of the frequency response functions shown by FIG. 1, each weighted by the corresponding product of particle number and scattering efficiency at that size. The demodulated signals are converted by the A/D converter 46 into digital signals and applied to the computing device 45 for processing. Since the demodulated signals are relatively linear, the particle size distribution measurement is easily produced by using an iterative constrained inversion algorithm, based on a theoretical model of particle motion in an oscillating dispersant.

Figure 1:
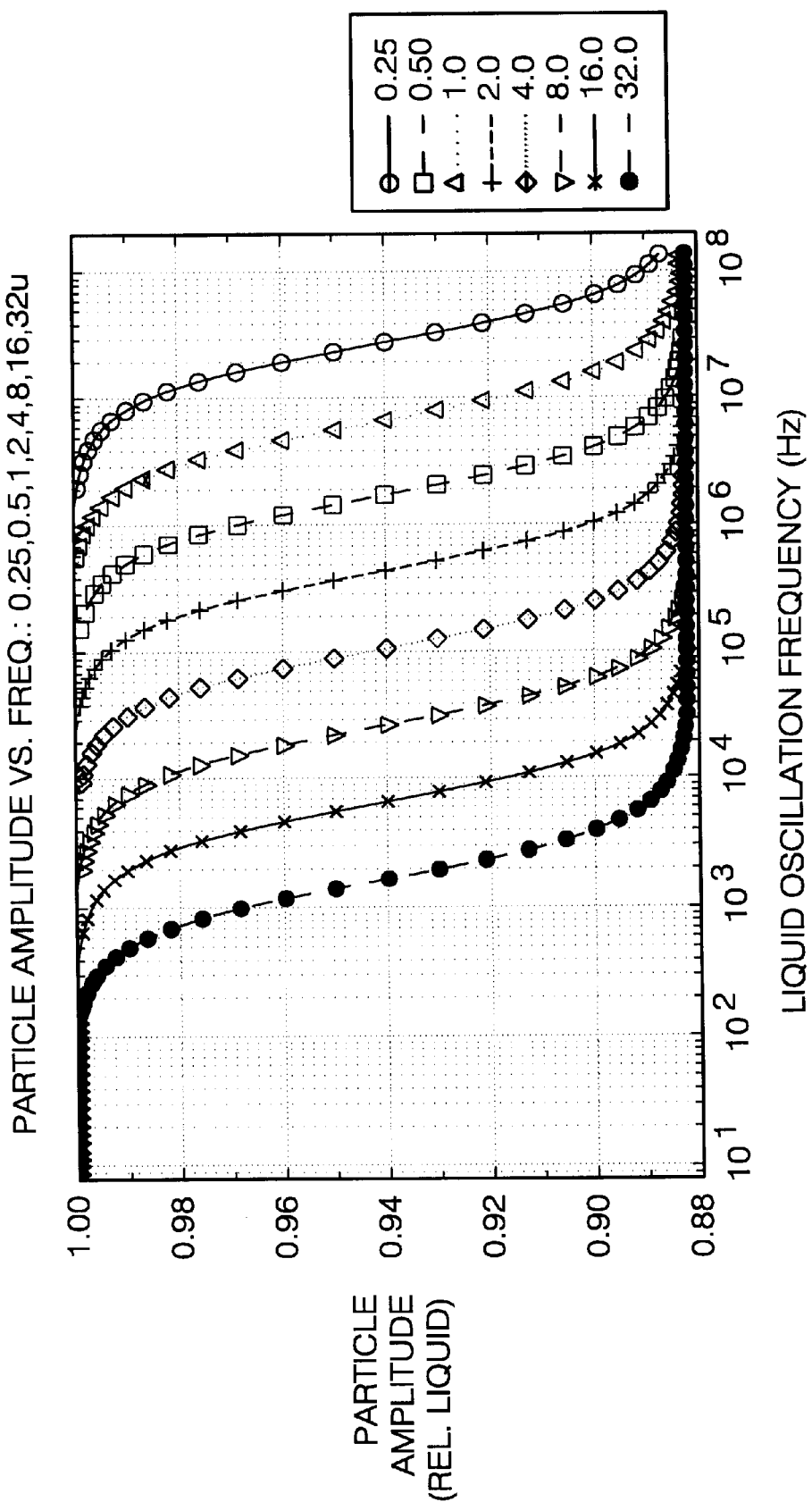
FIG. 1 illustrates, in the form of a graph plot, the particle amplitude of various particle sizes at various dispersant oscillation frequencies.

The distribution of relative velocity amplitude and phase between the particle ensemble and dispersant must be measured accurately to determine the particle size distribution. As shown in FIG. 1, the relative motion of a particle will be very small when the particle and dispersant densities are similar. In such cases, the homodyne (self-beating) power spectrum or autocorrelation function of the detector current is preferred in the measurement of particle motion amplitude and phase relative to the other particles in a particle ensemble rather than relative to the dispersant. Analysis of the homodyne spectrum will provide an accurate particle-to-particle relative velocity amplitude and phase distribution, which is then referenced to absolute velocity values by a heterodyne spectral measurement of the particle sample. Therefore, there is advantage in measuring separately both homodyne and heterodyne power spectra from the same particle dispersion, which is in a frequency scanned ultrasonic field flow.

Figure 5:
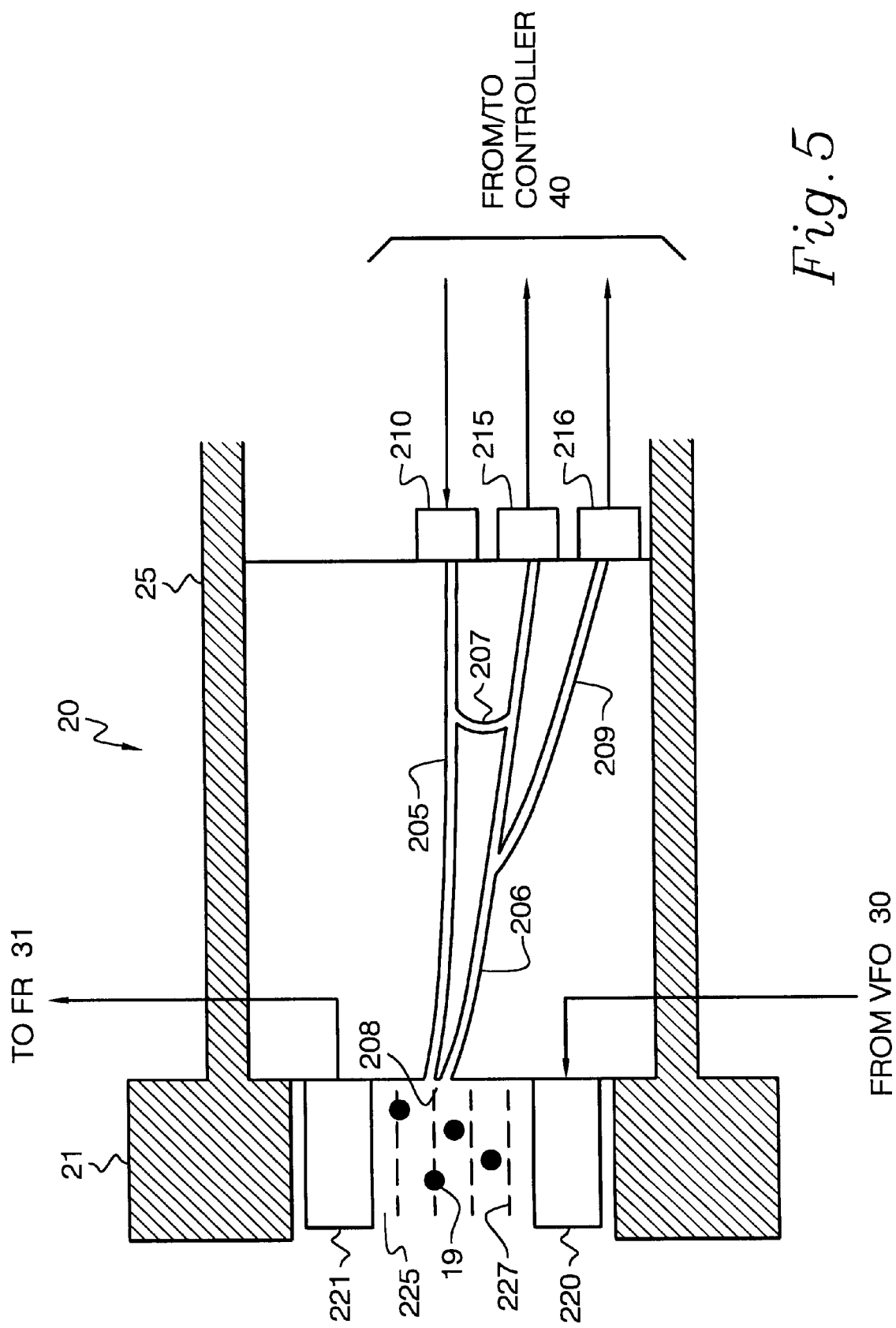
FIG. 5 depicts the second embodiment of the detector of the present invention.

Turning now to FIG. 5 of the included drawings, a second embodiment of the detection device of the present invention is illustrated that provides the advantages explained above. The optical detector 20 includes an integrated optic device 200 located internally within a housing 25 of the optical detector 20. The integrated optic device 200 further includes a laser diode 210 optically connected to a first optical waveguide 205. A second optical waveguide 206 is optically connected to a light detection device 215. Laser diode 210 and light detection device 215 are further electrically connected to controller 40. Optical waveguides 205 and 206 converge proximate to each other at point 208 located at an edge of the integrated optics device 200 and within head end 21. A third optical waveguide 209 is provided that couples the light energy in waveguide 206 to a second light detection device or photodetector 216. Photodetector 216 is comprised of a so-called sensitive photodetector such as an Avalanche Photodiode (APD) or Photon Multiplier (PM).

An ultrasonic transducer transmitter, such as a piezoelectric transducer 220, extends from integrated optics device 200 within head end 21. An ultrasonic transducer receiver 221 also extends from the integrated optic chip 200 that is in a spaced and facing relationship with the ultrasonic transducer transmitter 220, forming a detection area 225 therebetween. Transmitter 220 is electrically connected to VFO 30 which drives transmitter 220 at various frequencies from a few Hertz to the Megahertz range. The ultrasonic transducer receiver 221 is electrically connected to the FR 31 and is disposed to detect and track the amplitude and phase of the ultrasonic waves 227 transmitted into detection area 225. Ultrasonic waves 227 excite into oscillation any particles 19 that are contained within the detection area 225.

Figure 6:
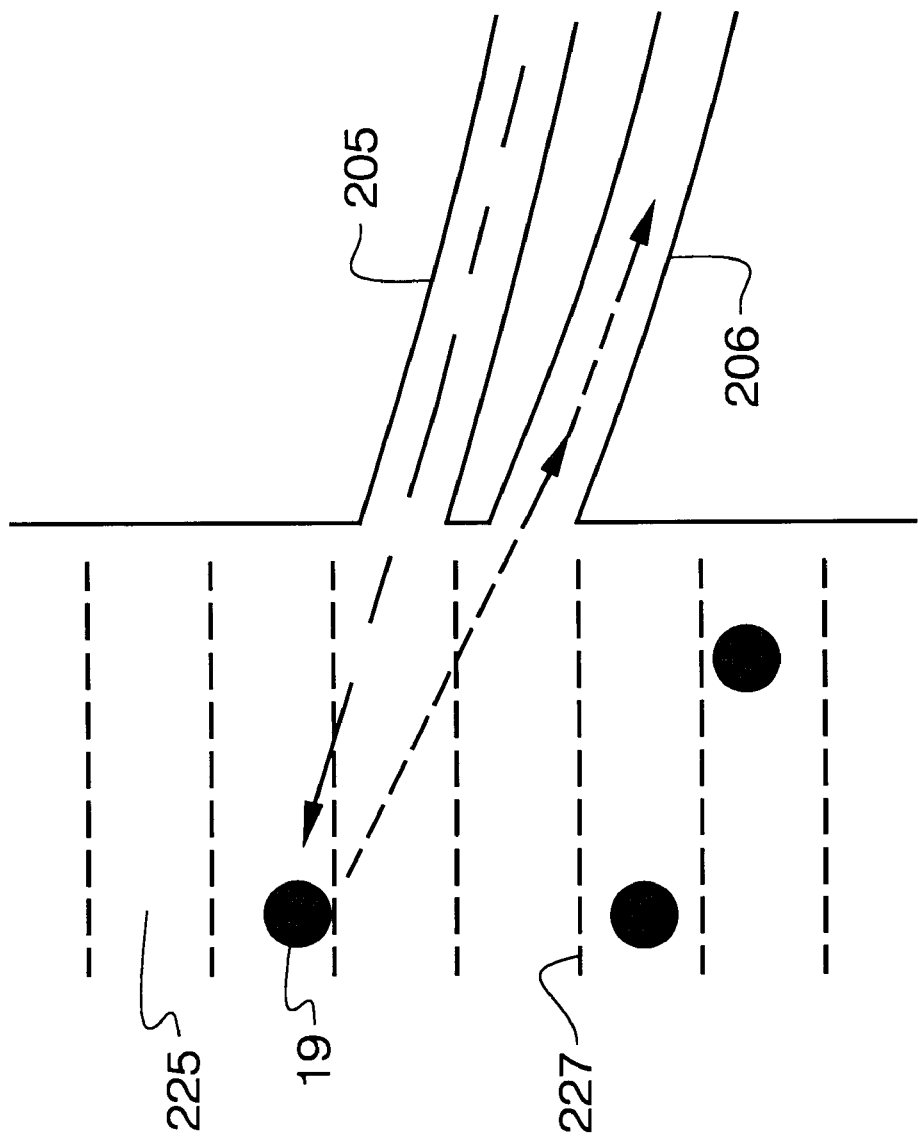
FIG. 6 depicts, in diagram view, the irradiation of the particles and collection of the scattered light energy from the particles in an oscillating flow field in accordance with the second embodiment of the present invention.

Turning to FIG. 6 as well as FIG. 5, the operation of the optical detector of the present invention will be explained. Upon the application of excitation voltage from controller 40, laser diode 210 produces light energy in a specific optical frequency range that is optically coupled into waveguide 205. The light energy coupled into waveguide 205 exits the waveguide from a first port at point 208 and is injected into the detection area 225 to irradiate the particles 19 that are in oscillation and contained therein. The Doppler shifted light scattered by the oscillating particles 19 is collected by waveguide 206 from a second port at point 208. As can be seen in FIGS. 5 and 6, waveguides 205 and 206 are oriented at an angle relative to the direction of the ultrasonic waves 227. This angular orientation of the first and second ports of waveguides 205 and 206, respectively, is made in order to provide particle velocity components that are perpendicular to equi-optical phase planes of the scattering configuration.

As with the detector of the first embodiment, the Doppler broadened spectrum of the scattered light conveyed by waveguide 206 must be mixed with the source light produced by laser diode 210. This is accomplished by optical loop 207. Optical loop 207 acts as a local oscillator to heterodyne or mix the laser source light from waveguide 205 (no Doppler frequency shift) with the Doppler-shifted scattered light collected by waveguide 206. This produces a down-shifted difference light spectrum similar to that commonly used in dynamic light scattering techniques. Additionally, the detector of this second embodiment splits off the scattered light energy from particles 19 before entering optical loop 207 and is conveyed to the third waveguide 209 for transmission to APD 216. The APD 216 measures the homodyne spectrum without mixing with the source light. The scattered light detected by photodetector 216 is applied as detector current to controller 40, where it is downshifted by mixing it with itself (self beating). The velocity and particle size information retrieved by the light detection device 215 is also passed as detector current to the controller 40, where it is demodulated at various ultrasonic excitation frequencies. The total demodulated particle velocity amplitude spectrum is the sum of the frequency response functions shown by FIG. 1, each weighted by the corresponding product of particle number and scattering efficiency at that size. The demodulated heterodyne and homodyne signals are converted by the A/D converter 46 into digital signals and applied to the computing device 45 for processing. Since the demodulated signals are relatively linear, the particle size distribution measurement is easily produced by using an iterative constrained inversion algorithm, based on a theoretical model of particle motion in an oscillating dispersant.

Alternatively, instead of measuring the scattered signal at each ultrasonic frequency sequentially, the entire frequency range may be measured concurrently by exciting the ultrasonic transducer transmitter with a broad band electronic signal or white noise. A spectrum analyzer could then be employed to analyze the entire scattering signal spectrum in order to measure the entire particle motion frequency. Essentially all of the individual ultrasonic frequencies would be excited together and their responses would be separated by spectral analysis of the scattered signal.

It will be understood by those skilled in the art that the embodiments of the present invention may be made with discrete optics that focus the source and scattered light through the surface of a window which contacts the dispersant in the sample cell. Additionally, the local oscillator coupler 107, 207 can also be effectively made using an optical beamsplitter; and the integrated optic waveguides and couplers could be replaced by suitable fiber optic conductors and fiber optic couplers.

The present invention has been described with particular reference to the preferred embodiments thereof. It will be obvious that various changes and modifications can be made therein without departing from the spirit and scope of the invention as defined in the appended claims.

What is claimed is:

1. A detector used in a system that determines the size distribution of particles contained in a dispersant medium comprising:
   a) means for exciting said dispersant medium at an ultrasonic frequency to cause said particles contained in said dispersant medium to oscillate at said ultrasonic frequency;
   b) a light source for producing light energy in a specific frequency range;
   c) first means for conveying said light energy from said light source to said dispersant medium;
   d) second means for capturing and conveying the light energy scattered by said particles in oscillation;
   e) third means for conveying light energy from said light source to said second means, producing heterodyned light energy; and
   f) a light energy detection device optically connected to said second means receiving said heterodyned light energy, whereby responsive to said heterodyned light energy said light energy detection device produces signals representative of the heterodyned light energy detected.

2. The detector as claimed in claim 1 wherein said means for exciting said dispersant medium excites said dispersant medium using a plurality of ultrasonic frequencies applied sequentially to said dispersant medium and for each ultrasonic frequency heterodyned light energy is produced and applied to said light energy detection device, whereby said light energy detection device produces signals representative of each ultrasonic frequency applied.

3. The detector as claimed in claim 2 wherein said means for exciting said dispersant medium includes an ultrasonic transmitter and an ultrasonic receiver located in a spaced and facing relationship to each other and both immersed substantially within said dispersant medium, forming therebetween a detection area, whereby said ultrasonic transmitter injects ultrasonic energy into said detection area, causing said particles found therein to oscillate at the frequency of the injected energy and said ultrasonic receiver detects the phase and amplitude of the ultrasonic energy traversing the detection area.

4. The detector as claimed in claim 3 wherein said first means for conveying light energy is a first light guide optically coupled to said light source on one end and in contact with said detection area on a second end, said first light guide arranged to convey said light energy from said light source to said detection area, whereby said light energy is transmitted into said detection area, irradiating the particles in oscillation found therein.

5. The detector as claimed in claim 4 wherein said second means for capturing light energy is a second light guide having a first end in contact with said detection area and located adjacent said first light guide second end, said second light guide further including a second end optically connected to said light energy detection device, said second light guide arranged to capture the light energy scattered by said particles in oscillation in said detection area, coupling said captured scattered light energy into said second light guide.

6. The detector as claimed in claim 5 wherein said third means for conveying light energy is a third light guide having a first end optically coupled to said first light guide between said first light guide first and second ends arranged to receive therein said light energy from said light source, said third light guide further including a second end optically coupled to said second light guide, transmitting the light energy conveyed therein to said second light guide, whereby said light energy from said light source is mixed with the scattered light energy captured by said second light guide producing said heterodyned light energy and said heterodyned light energy is conveyed by said second light guide to said light energy detection device.

7. The detector as claimed in claim 6 wherein said detector further includes a housing and said light source, said first light guide, said second light guide, said third light guide and said light detection device are housed within said housing.

8. The detector as claimed in claim 7 wherein said housing further includes a head end and said ultrasonic transmitter, said detection area and said ultrasonic receiver are housed within said head end, and said head end is substantially immersed within said dispersant medium.

9. The detector as claimed in 7 wherein said light source, said first light guide, said second light guide, said third light guide and said light detection device are a monolithic structure arranged as an integrated optical device and said integrated optical device is housed within said housing.

10. A detector used in a system that determines the size distribution of particles contained in a dispersant medium comprising:
    a) a housing having a head end, said head end substantially immersed in said dispersant medium;
    b) means for exciting said dispersant medium at an ultrasonic frequency housed within said head end arranged to cause said particles contained in said dispersant medium to oscillate at said ultrasonic frequency;
    c) a monolithic optical device housed within said housing including a light source that produces light energy in a specific frequency range, a first light guide optically coupled to said light source conveying said light energy from said light source to said head end and into said dispersant medium, a second light guide that captures and conveys within said second light guide the light energy scattered by said particles in oscillation, and a third light guide optically coupled to said first light guide and to said second light guide, conveying said light energy from said light source to said second light guide producing heterodyned light energy; and d) a light energy detection device optically connected to said second light guide receiving said heterodyned light energy, whereby, responsive to said heterodyned light energy, said light energy detection device produces signals representative of the heterodyned light energy detected.

11. A detector used in a system that determines the size distribution of particles contained in a dispersant medium comprising:

a) means for exciting said dispersant medium at an ultrasonic frequency to cause said particles contained in said dispersant medium to oscillate at said ultrasonic frequency;

b) a light source for producing light energy in a specific frequency range;

c) first means for conveying said light energy from said light source to said dispersant medium;

d) second means for capturing and conveying the light energy scattered by said particles in oscillation;

e) third means for conveying light energy from said light source to said second means producing heterodyned light energy;

f) fourth means for receiving the light energy captured by said second means;

g) a first light energy detection device optically connected to said second means receiving said heterodyned light energy, whereby, responsive to said heterodyned light energy, said first light energy detection device produces first signals representative of the heterodyned light energy detected; and h) a second light energy detection device optically connected to said fourth means receiving said light scattered by said particles in oscillation, whereby, responsive to receiving said light scattered by said particles, said detection device produces second signals representative of the scattered light detected.

12. The detector as claimed in claim 11 wherein said means for exciting said dispersant medium excites said dispersant medium using a plurality of ultrasonic frequencies applied sequentially to said dispersant medium and for each ultrasonic frequency heterodyned light energy is produced and applied to said light energy detection device, whereby said light energy detection device produces signals representative of each ultrasonic frequency applied.

13. The detector as claimed in claim 12 wherein said means for exciting said dispersant medium includes an ultrasonic transmitter and an ultrasonic receiver located in a spaced and facing relationship to each other, both immersed substantially within said dispersant medium, forming therebetween a detection area, whereby said ultrasonic transmitter injects ultrasonic energy into said detection area, causing said particles found therein to oscillate at the frequency of the injected energy and said ultrasonic receiver detects the phase and amplitude of the ultrasonic energy traversing the detection area.

14. The detector as claimed in claim 13 wherein said first means for conveying light energy is a first light guide optically coupled to said light source on one end and in contact with said detection area on a second end, said first light guide arranged to convey said light energy from said light source to said detection area, whereby said light energy is transmitted into said detection area, irradiating the particles in oscillation found therein.

15. The detector as claimed in claim 14 wherein said second means for capturing light energy is a second light guide having a first end in contact with said detection area and located adjacent said first light guide second end, said second light guide further including a second end optically connected to said light energy detection device, said second light guide arranged to capture the light energy scattered by said particles in oscillation in said detection area, coupling said captured scatter light energy into said second light guide.

16. The detector as claimed in claim 15 wherein said third means for conveying light energy is a third light guide having a first end optically coupled to said first light guide between said first light guide first and second ends arranged to receive therein said light energy from said light source, said third light guide further including a second end optically coupled to said second light guide, transmitting the light energy conveyed therein to said second light guide, whereby said light energy from said light source is mixed with the scattered light energy captured by said second light guide producing said heterodyned light energy and said heterodyned light energy is conveyed by said second light guide to said first light energy detection device.

17. The detector as claimed in claim 16, wherein said fourth means is a fourth light guide having a first end optically connected to said second light guide between said second light guide second end and said third light guide, said fourth light guide further including a second end optically connected to said second light energy detection device, whereby said scatter light energy conveyed by said second light guide is additionally coupled into said fourth light guide and conveyed to said second light energy detection device.

18. The detector as claimed in claim 17, wherein said first light guide second end and said second light guide second end are oriented obliquely to the vertical plane of the detection area and said light energy is injected into said detection area obliquely to the ultrasonic energy waves injected into said detection area by said ultrasonic transmitter.

19. The detector as claimed in claim 18 wherein said detector further includes a housing and said light source, said first light guide, said second light guide, said third light guide, said fourth light guide and said first and second light detection devices are housed within said housing.

20. The detector as claimed in claim 18 wherein said housing further includes a head end and said ultrasonic transmitter, said detection area and said ultrasonic receiver are housed within said head end, and said head end is substantially immersed within said dispersant medium.

21. The detector as claimed in 19 wherein said light source, said first light guide, said second light guide, said third light guide, said fourth light guide and said first and second light detection devices are a monolithic structure arranged as an integrated optical device and said integrated optical device is housed within said housing.

22. The detector as claimed in claim 21 wherein said second light detection device is an Avalanche Photodiode (APD).

23. The detector as claimed in claim 21 wherein said second light detection device is a Photon Multiplier (PM).

24. The detector as claimed in claim 1 wherein said means for exciting said dispersant medium excites said dispersant medium using a plurality of ultrasonic frequencies applied concurrently to said dispersant medium, whereby heterodyned light energy is produced and applied to said light energy detection device and said light energy detection device produces signals representative of said plurality of said ultrasonic frequency applied to said dispersant medium.

25. The detector as claimed in claim 11 wherein said means for exciting said dispersant medium excites said dispersant medium using a plurality of ultrasonic frequencies applied concurrently to said dispersant medium whereby heterodyned light energy is produced and applied to said light energy detection device and said light energy detection device produces signals representative of said plurality of said ultrasonic frequency applied to said dispersant medium.

\* \* \* \* \*